(12) United States Patent
Kerschner et al.

(10) Patent No.: US 8,104,322 B2
(45) Date of Patent: Jan. 31, 2012

(54) METHOD OF WORKING IN PRESSING DIES USING MARKING PAINT

(75) Inventors: Ing. Matthias Kerschner, Rohrbach (DE); Josef Hollerbach, Landshut (DE)

(73) Assignee: Audi AG, Ingolstadt (DE)

( * ) Notice: Subject to any disclaimer, the term of this patent is extended or adjusted under 35 U.S.C. 154(b) by 737 days.

(21) Appl. No.: 12/196,197

(22) Filed: Aug. 21, 2008

(65) Prior Publication Data
US 2009/0044585 A1     Feb. 19, 2009

(51) Int. Cl.
*B21D 37/01*     (2006.01)
*B21K 5/20*     (2006.01)

(52) U.S. Cl. ............... 72/462; 72/37; 72/340; 76/107.1

(58) Field of Classification Search ............... 72/37, 46, 72/462, 476, 340, 343, 347, 379.2; 76/107.1, 76/107.4
See application file for complete search history.

(56) References Cited

U.S. PATENT DOCUMENTS

| | | | | |
|---|---|---|---|---|
| 3,129,612 A | * | 4/1964 | Anneren et al. | 76/107.1 |
| 3,172,209 A | | 3/1965 | Reichart | |
| 3,636,797 A | * | 1/1972 | Moore | 76/107.1 |
| 4,326,981 A | * | 4/1982 | Molina | 252/301.19 |
| 5,243,194 A | * | 9/1993 | Sano et al. | 250/461.1 |
| 5,584,216 A | * | 12/1996 | Sinjen | 83/62.1 |
| 6,471,887 B2 | * | 10/2002 | Oshima et al. | 252/301.16 |
| 6,949,205 B2 | * | 9/2005 | Pendergrass | 252/301.36 |

FOREIGN PATENT DOCUMENTS

| | | |
|---|---|---|
| DE | 10 43 858 C | 3/1939 |
| DE | 43 11 154 A1 | 11/1994 |
| DE | 102 44 819 A1 | 4/2004 |
| GB | 672 763 A | 5/1952 |
| JP | 2000-334584 | * 12/2000 |

* cited by examiner

*Primary Examiner* — Edward Tolan
(74) *Attorney, Agent, or Firm* — Novak Druce + Quigg LLP

(57) ABSTRACT

The method according to the invention for working in pressing dies using marking paint wherein a fluorescent marking paint is used. This enables the operator in the manual working in of pressing dies to identify the painted tool surface without error and error-free detection of the tool surface occupied by marking paint is also possible by means of suitable devices (camera) for working-in of the pressing die which is done more or less automated.

3 Claims, No Drawings

METHOD OF WORKING IN PRESSING DIES USING MARKING PAINT

CROSS-REFERENCE TO RELATED APPLICATIONS

This application claims priority from German Patent Application No. 102006008189.7 filed Feb. 22, 2006

The invention relates to a method of working in pressing dies using marking paint.

BACKGROUND OF THE INVENTION

In the production of deep drawing tools for sheet metal parts of motor vehicle bodies, for example, generally finish-working or remachining of tool surfaces takes place in order to prevent overly high local surface pressure on the sheet metal parts of the vehicle body during a deep drawing process. This could be a contributory cause of crack formation. Therefore, for example, for finishworking of the tool surfaces in a so-called marking process the surface regions of the tools to be remachined can be identified and then, for example, can be removed by scraping or grinding.

Thus, for example DE 43 11 154 C2 discloses a device and a method, in which in a first working step for identifying the surface region of a tool surface to be remachined first the sheet metal part is painted with marking paint. The sheet metal is inserted into a spotting press and pressed or deep drawn between the two halves of the tool. Using the paint impression of the marked sheet metal part on the respective tool surface the surface regions with overly high surface pressure can be identified. Surface regions with a paint impression of high color intensity apply an overly high surface pressure and must be remachined in a second working step by the corresponding surface machining.

For efficient use of the spotting press, finishworking of the identified regions of the tool surfaces generally is done outside the spotting press. In this way the occupancy of the spotting press is limited to the actual marking process, saving time. The tool surface after the marking process, as already mentioned, is further machined by scraping or grinding in manual finishworking. This surface treatment is on the one hand time-consuming, on the other hand machining of the identified surface regions, in particular the amount of vertical removal, is subject to the subjective assessment of the respective operator. As a result of the mirror-like metallic surface, optical detection of the tool surface in daylight or factory light is not possible without errors (reflections) so that the work result can also be adversely affected thereby.

There have already been efforts to automate the process of working in a pressing die or shaping tool as much as possible, as can be derived, for example, from the older application 10 2006 001 712.9 of the applicant. A device for finishworking a shaping tool is described there; it has a machining means which electronically detects the paint impression on the tool surface and depending on the intensity of the paint impression determines the location and/or dimension of the surface region to be remachined and remachines it accordingly. The machining device also has an analysis unit which preferably optically detects the tool surface with the paint impression and generates the corresponding image data of the tool surface.

The object of the invention is to further optimize the procedure of working in pressing dies using marking paint such that both with respect to manual working-in and also with respect to largely automated working-in, error-free optical detection of the tool surface and the marking paint is possible.

SUMMARY OF THE INVENTION

The solution according to the invention lies in the use of fluorescent marking paint.

Devices and methods for detection of a fluorescent substance on a technical surface are conventional prior art, as follows from DE 102 44 819 A1. A device and a method are described there for detection of at least one material layer located on a technical surface with at least one light source which illuminates the technical surface and which emits a light beam pointed at the material layer with a wavelength which excites the material layer to fluorescent radiation, there being at least one detector unit which receives the fluorescent radiation and furthermore there being an evaluation unit which undertakes qualitative material determination of the fluorescent material layer depending on the fluorescent radiation. Indications of the present application, however, cannot be derived from this prior art.

DETAILED DESCRIPTION OF THE PREFERRED EMBODIMENT OF THE INVENTION

The use of a fluorescent paint according to the invention is advantageously supplemented by using black or UV light in order to illuminate the tool surface free of reflections. The fluorescent marking paint is advantageously a mixture of the dye uranine (fluorescein-disodium salt) $Na_2C_{20}H_{10}O_5$ and any carrier substance which is soluble or insoluble in water. If, moreover, this marking paint is exposed to black or UV light, as a yellow, luminous contour the marking spot contrasts with the remainder of the tool surface in an especially distinct and easily detectable manner.

The carrier substance itself can be freely chosen depending on the application and can be varied in density as desired. For the application of marking, the consistency should be chosen to be somewhat more viscous in order not to adulterate the marking image by running of the paint.

The invention claimed is:

1. A method of restoring a selected surface contour of a tool of a machine operable to press form configured finished parts from planar sheet metal, comprising:
   applying a fluorescent marking paint on a surface of a planar sheet metal part;
   inserting said painted sheet metal part in said machine with the painted surface thereof facing said tool surface;
   operating said machine to press form said painted sheet metal part and thus cause said paint to transfer and mark high spots on said tool surface;
   removing said formed part;
   optically scanning paint transferred to said high spots and recording a pattern thereof; and
   removing said high spots by guiding a cutting tool over said tool surface corresponding to said recorded pattern.

2. A method according to claim 1 including irradiating said marked tool surface with ultraviolet light.

3. A method according to claim 1 wherein said marking paint consists of a mixture of the dye uranin ($Na_2C_{20}H_{10}O_5$) and any carrier substance which is soluble or insoluble in water.

* * * * *